US010345201B2

(12) United States Patent
Ghiasvand et al.

(10) Patent No.: US 10,345,201 B2
(45) Date of Patent: Jul. 9, 2019

(54) POLYPYRROLE/GRAPHENE OXIDE NANOCOMPOSITE-COATED FIBER LOCATED IN A CAPILLARY TUBE REINFORCED BY A VACUUM SYSTEM FOR ASSESSMENT OF OXIDATIVE STABILITY OF EDIBLE OILS

(71) Applicants: Alireza Ghiasvand, Khoramabad (IR); Mina Behfar, Khuzestan (IR); Fatemeh Yazdankhah, Khoramabad (IR)

(72) Inventors: Alireza Ghiasvand, Khoramabad (IR); Mina Behfar, Khuzestan (IR); Fatemeh Yazdankhah, Khoramabad (IR)

(*) Notice: Subject to any disclaimer, the term of this patent is extended or adjusted under 35 U.S.C. 154(b) by 0 days.

(21) Appl. No.: 15/688,173

(22) Filed: Aug. 28, 2017

(65) Prior Publication Data

US 2018/0038777 A1    Feb. 8, 2018

(51) Int. Cl.
*G01N 1/22* (2006.01)
*B01J 20/28* (2006.01)
(Continued)

(52) U.S. Cl.
CPC .......... *G01N 1/2214* (2013.01); *B01J 20/20* (2013.01); *B01J 20/261* (2013.01);
(Continued)

(58) Field of Classification Search
CPC ........ G01N 30/12; G01N 30/54; G01N 30/06; G01N 30/482; G01N 1/14; G01N 1/22; G01N 1/2214; G01N 1/2294; G01N 2030/009; G01N 2030/025; G01N 2030/027; G01N 2030/062; G01N 2030/121; G01N 2030/484; G01N 2030/488; G01N 33/24; G01N 2001/2229;
(Continued)

(56) References Cited

U.S. PATENT DOCUMENTS 4,014,797 A    3/1977  Raines
4,732,046 A *  3/1988  Lawrence ............ G01N 1/4022
                                                250/282

(Continued)

OTHER PUBLICATIONS

Xu et al. ("Hydrofluoric Acid Etched Stainless Steel Wire for Solid-Phase Microextraction"), Analytical Chemistry, vol. 81, No. 12, Jun. 15, 2009, pp. 4971-4977 (Year: 2009).*

(Continued)

*Primary Examiner* — Lisa M Caputo
*Assistant Examiner* — Suman K Nath
(74) *Attorney, Agent, or Firm* — NovoTechIP International PLLC

(57) ABSTRACT

A vacuum-assisted coated fiber located in a capillary tube system for sampling and delivering materials to an analytical device and a method for sampling analytes is disclosed. A sorbent comprising polypyrrole/graphene oxide is coated on a fiber inserted within an interior space of the capillary tube to entrap an analyte within a sample. The vacuum-assisted coated fiber located in a capillary tube device also includes a vacuum device configured to vacuum the extraction vial. This may improve the extraction of the analytes vapors from the sample, matrix to the sorbent bed.

8 Claims, 7 Drawing Sheets

(51) Int. Cl.
| | |
|---|---|
| *B01J 20/32* | (2006.01) |
| *G01N 1/40* | (2006.01) |
| *G01N 33/03* | (2006.01) |
| *G01N 30/06* | (2006.01) |
| *G01N 30/14* | (2006.01) |
| *B01J 20/26* | (2006.01) |
| *B01J 20/20* | (2006.01) |
| *B01J 20/30* | (2006.01) |
| *G01N 30/02* | (2006.01) |
| *G01N 30/12* | (2006.01) |

(52) U.S. Cl.
CPC ... *B01J 20/28007* (2013.01); *B01J 20/28028* (2013.01); *B01J 20/3085* (2013.01); *B01J 20/3204* (2013.01); *B01J 20/3214* (2013.01); *B01J 20/3293* (2013.01); *G01N 1/2226* (2013.01); *G01N 1/405* (2013.01); *G01N 30/06* (2013.01); *G01N 30/14* (2013.01); *G01N 33/03* (2013.01); *G01N 2001/2229* (2013.01); *G01N 2030/025* (2013.01); *G01N 2030/065* (2013.01); *G01N 2030/126* (2013.01); *G01N 2030/128* (2013.01); *G01N 2030/143* (2013.01)

(58) Field of Classification Search
CPC ............... G01N 1/405; B01J 20/28007; B01J 20/28028; B01J 20/3214; B01J 20/3293
USPC ........... 73/23.35–23.42, 31.07, 61.52–61.61, 73/64.56, 863.12; 210/656–659; 96/101–107, 112, 143–146; 422/69, 70, 422/88, 89
See application file for complete search history.

(56) References Cited

U.S. PATENT DOCUMENTS

| | | | |
|---|---|---|---|
| 5,064,418 | A | 11/1991 | Cronin |
| 6,405,608 | B1* | 6/2002 | Lindgren ................ F41H 11/12 73/863.21 |
| 7,057,168 | B2 | 6/2006 | Miller |
| 7,749,443 | B2 | 7/2010 | Land |
| 8,598,325 | B2 | 12/2013 | Pawliszyn |
| 2005/0118599 | A1 | 6/2005 | Pawliszyn |
| 2007/0056360 | A1 | 3/2007 | Grant |
| 2009/0308811 | A1 | 12/2009 | Tepper |
| 2013/0233054 | A1 | 9/2013 | Oliphant et al. |
| 2014/0318274 | A1 | 10/2014 | Zimmerman |
| 2015/0233655 | A1 | 8/2015 | Ghiasvand |
| 2016/0320271 | A1 | 11/2016 | Schueler |
| 2017/0059533 | A1 | 3/2017 | Ghiasvand |
| 2017/0184554 | A1* | 6/2017 | Ghiasvand ........... G01N 30/482 |
| 2018/0038777 | A1 | 2/2018 | Ghiasvand |

OTHER PUBLICATIONS

Jafari et al. ("Solid-phase microextraction of phthalate esters by a new coating based on a thermally stable polypyrrole/graphene oxide composite"), Journal of Separation Science, vol. 37, Issue 21, Aug. 2014. (Year: 2014).*

Li et al. ("Fabrication of Polypyrrole/Graphene Oxide Composite Nanosheets and Their Applications for Cr(VI) Removal in Aqueous Solution"), PLOS ONE, Aug. 2012, vol. 7, Issue 8, e43328). (Year: 2012).*

Non-Final Office Action Issued in U.S. Appl. No. 15/083,206, dated Mar. 22, 2018, 23 Pages.

Non-Final Office Action Issued in U.S. Appl. No. 15/402,120, dated Mar. 29, 2018, 11 Pages.

\* cited by examiner

POLYPYRROLE/GRAPHENE OXIDE NANOCOMPOSITE-COATED FIBER LOCATED IN A CAPILLARY TUBE REINFORCED BY A VACUUM SYSTEM FOR ASSESSMENT OF OXIDATIVE STABILITY OF EDIBLE OILS

CROSS-REFERENCE TO RELATED APPLICATION

This application claims the benefit of priority to an Iran Application Serial Number 139550140003006862, filed on Aug. 28, 2016, entitled "Polypyrrole/graphene oxide nanocomposite coated fiber located in a capillary tube reinforced by a vacuum system for assessment of oxidative stability of edible oils" and issued as Iran Patent Number 88933, the entire content of which is incorporated herein by reference.

BACKGROUND

Oxidation is the main reason for instability of the edible oils and causes change in chemical and nutritional properties of the oils. Aldehydes are amongst the products of the oxidation and are well-known for being health risks. The commercial methods to oxidation-stabilize the edible oils are time consuming, expensive and demand preparation. Moreover, using toxic and reactive chemical compounds and solvents are other disadvantages of these methods. Solid-phase microextraction (SPME) is a new technique which eliminates the need for such harmful solvents and compositions. However, one of the main drawbacks of the SPME methods is the cost-prohibitive, brittle fibers that are used as sorbents. The present application discloses a polypyrrolelgraphene oxide nanocomposite coated fiber located in a capillary tube reinforced by vacuum system for assessment of oxidative stability of edible oils.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one implementation, the present disclosure is directed to a vacuum-assisted coated fiber located in a capillary tube (VA-CFLCT) system. The system includes a first capillary tube including a first end and a second end, a second capillary tube disposed adjacent to the first capillary tube, and a stainless-steel fiber disposed in an interior space of the first capillary tube. Furthermore, the system includes an extraction vial including a first opening and a second opening where the extraction vial is configured to extract an analyte. In addition, the system includes a sorbent coated on the stainless-steel fiber that is configured to entrap the analyte, where the analyte is attached to a sample that is injected into the extraction vial. In addition, a first cover is configured to cover the first opening of the extraction vial, where the first cover includes a first aperture, a second aperture, and a third aperture. The first aperture is configured to receive the first capillary tube within an interior space of the extraction vial, the second aperture is configured to receive the second capillary tube within the interior space of the extraction vial, and the third aperture is configured to receive a hollow needle for injecting the sample into the extraction vial. A peristaltic pump including an inlet and an outlet is also included in the system, where the inlet is coupled to both the second end of the first capillary tube and a second end of the second capillary tube, and the peristaltic pump is configured to circulate the extracted analyte though the first capillary tube and the second capillary tube to improve analyte adsorption on the sorbent inside the first capillary tube. The system can also include a vacuum device configured to evacuate the interior space of the extraction vial and improve the efficiency of the analyte extraction process, where the vacuum device includes a valve and a vacuum pump, where a connection tube connects the vacuum pump to the second opening of the extraction vial, where the vacuum pump is in fluid communication the extraction vial and is configured to provide a vacuum within the interior space of the extraction vial, and where the valve is configured to operate between an open position and a closed position. The closed position the valve disables the communication between the vacuum pump and the extraction vial and in the open position the valve enables the communication between the vacuum pump and the extraction vial.

In another aspect, the present disclosure is directed to a method for sampling analytes comprising synthesizing a nanosorbent, applying the nanosorbent as a coating on at least a portion of a stainless-steel fiber, thereby producing a nanosorbent-coated stainless-steel fiber, inserting the nanosorbent-coated stainless-steel fiber into a first capillary tube. The method also includes inserting a first end of the first capillary tube into a first end of a vacuum flask via a first aperture, inserting a first end of a second capillary tube into the first end of the vacuum flask via a second aperture, inserting a hollow needle into the first end of the vacuum flask via a third aperture, securing a second end of the first capillary tube to a peristaltic pump, and securing a second end of the second capillary tube to the peristaltic pump. In addition, the method involves securing a first end of a valve to a second end of the vacuum flask, the being valve configured to control a vacuum process, the valve including an open position and a closed position, securing a second end of the valve to a vacuum pump, creating a vacuum inside the vacuum flask by turning on the vacuum pump and switching the valve to the open position, and switching the valve to the closed position and turning the vacuum pump off, thereby maintaining the vacuum inside the vacuum flask. Furthermore, the method includes injecting a sample into the vacuum flask via the hollow needle and circulating the headspace (containing the analytes that released from sample matrix) inside the first capillary tube and the second capillary tube by use of the peristaltic pump.

Other systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
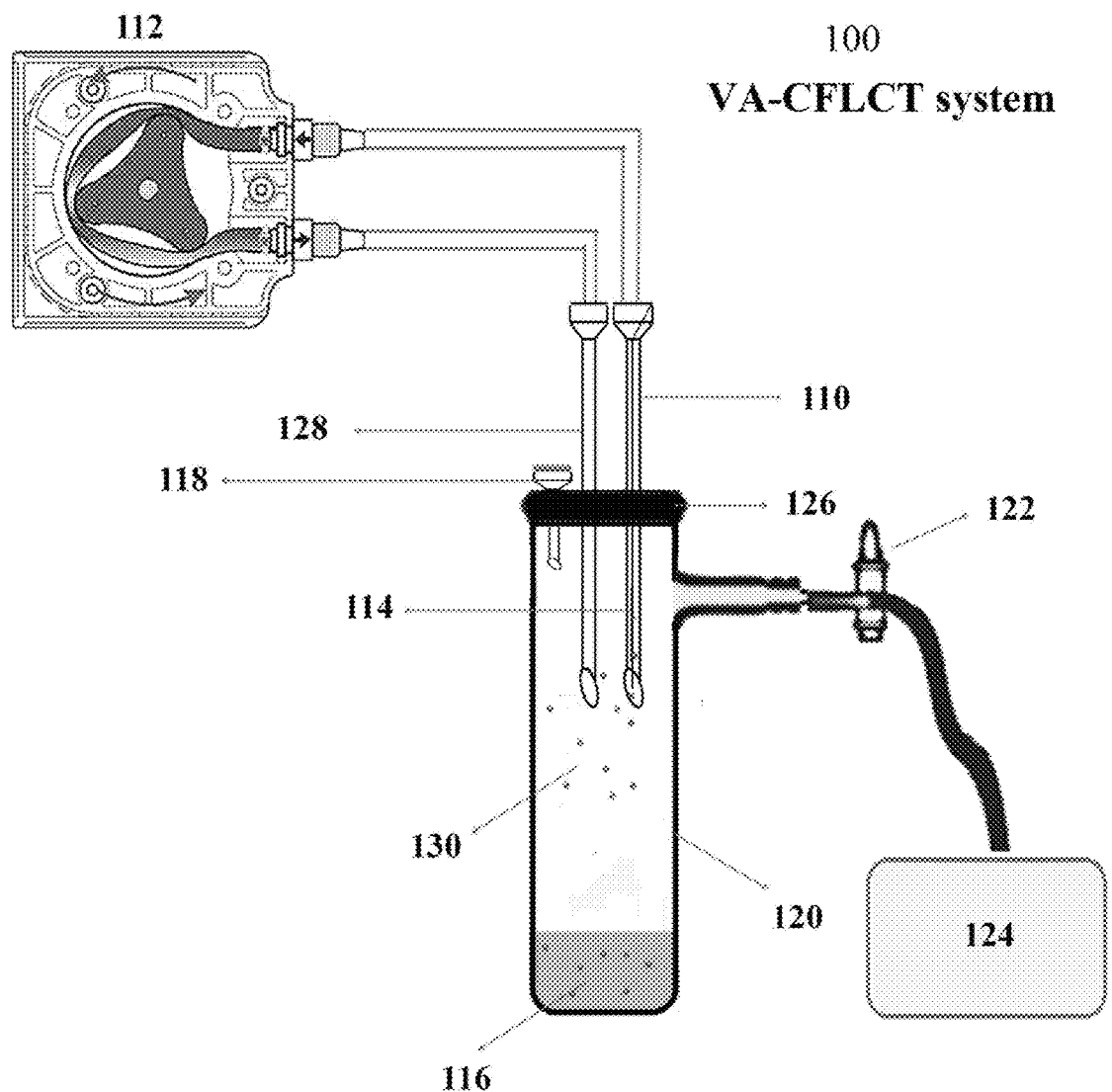
FIG. 1 illustrates a vacuum-assisted coated fiber located in a capillary tube device in accordance with one implementation of the instant application.

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings. The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

This application relates generally to a vacuum-assisted coated fiber located in a capillary tube (VA-CFLCT) device for sampling that can be used to extract analyte from complicated solid or liquid samples and deliver the extracted analyte to a gas chromatography (GC) system. More specifically, the application discloses a vacuum system to assist and enhance the extraction of the analyte.

The chief method of analyzing trace volatile chemicals has been solid-phase microextraction (SPME), which employs a fiber to collect the analyte and inject it into a gas chromatograph (GC) or liquid chromatograph (LC). This results in the capture and injection of only small quantities of the analytes and thus yields poor sensitivity. It was discovered that if large quantities of vapor or liquid analyte were drawn through a treated sorbent, the components of interest would be concentrated. Solvents were used to selectively remove the analyte from the sorbent, and a small portion of the solvent containing the analytes was then injected into the GC or LC. Concentration of the sample via a sorbent was an improvement in sensitivity over straight analyte injection, but it added many processing steps to the analysis, which could increase errors.

The instant application describes a polypyrrole/graphene oxide nanocomposite coated fiber located in a capillary tube reinforced by a vacuum system, and may also be referred to as a VA-CFLCT. In one implementation, the VA-CFLCT device can be configured to sample and deliver analyte to an analytical device, such as a gas chromatograph. The capillary tube may comprise a size similar to gas chromatographic injection needles. Furthermore, a sorbent bed is deposited on a stainless-steel wire, and fiber is inserted inside the capillary tube, which are used for extraction of samples. This is followed by thermal desorption into GC systems. All analytes, including those freely dissolved in the headspace gas as well as those associated with particulate matter entrained in the sample, may be extracted by the devices. Additional details with respect to the method and apparatus are provided below.

In one implementation, the sorbent is synthesized in-situ via a 2-electrode electrochemical polymerization/electrophoretic deposition method on a stainless-steel wire. The wire is then inserted into the capillary tube. For desorption, the capillary tube is inserted into a hot injector of the gas chromatograph. A vacuum-assisted coated fiber located in a capillary tube (VA-CFLCT) device may be used for either spot (grab) sampling or integrated (time-weighted-average) sampling. For spot sampling, a gas tight syringe or gas sampling pump may be connected to the free end of the capillary tube and used to draw a pre-defined sample volume through the capillary tube. The analytes' concentration is determined by determining the amount desorbed and dividing by the sample volume.

With respect to other gas sampling sorbent tubes, sampling rate and volume should be standardized and minimum breakthrough volume should be determined for the target sample during a method development. Instrumentation to facilitate automated processing of the VA-CFLCT device is commercially available for both desorption of a multiple field-sampled VA-CFLCT device and automated extraction and desorption from sample vials. Automated processing also simplifies the method development and the resulting workstations may be compatible with a variety of gas chromatographic instruments.

The vacuum-assisted coated fiber located in a capillary tube (VA-CFLCT) device may be more robust than solid-phase micro-extraction (SPME). The VA-CFLCT may also be an efficient particle filter and have a higher sorbent capacity, which allows it to perform exhaustive extraction(s). Depending on the degree of particle loading in the sample, the devices may here-used from a few to dozens of times. To date, the VA-CFLCT device has been used primarily for environmental analysis and breath analysis but is amenable to application for additional analytical chemistry applications.

FIG. 1 illustrates a vacuum-assisted coated fiber located in a capillary tube (VA-CFLCT) system ("system") 100 in accordance with one implementation of the instant application. The system 100 may include a first capillary tube which comprises a coated fiber located in a capillary tube device ("CFLCT device") 110, a peristaltic pump 112, a nanosorbent 114, a sample matrix 116, a sample injection site 118, an extraction vial 120, a two-way valve 122, a vacuum pump device 124, a silicon septum ("the first cover") 126 and a second capillary tube 128. The second capillary tube 128 can be substantially empty or unfilled. Furthermore, the analytes can evaporate under a reduced pressure condition, represented by vapors 130.

As shown in FIG. 1, the CFLCT device 110 includes an upper end or "first end" and a lower end or "second end". In one implementation, the CFLCT device 110 comprises a stainless steel fiber. As indicated above, the first capillary tube is disposed within the CFLCT device 100. The first end of the first capillary tube of the CFLCT device 110 may be configured to engage with the peristaltic pump 112. In addition, the second end of the first capillary fiber of the CFLCT device 110 can be configured to be inserted inside the extraction vial 120 in some implementations. The extraction vial is configured to extract analyte(s) in different implementations.

Furthermore, in some implementations, the vacuum pump 124 may be attached to the extraction vial 120 through a valve, such as the two-way valve 122. In one implementation, the two-way valve 122 is configured to control the vacuum. In different implementations, the sample matrix 116 may be inserted into the extraction vial 120 through a sample injection site 118. In one implementation, the extraction vial includes a first opening and a second opening.

Thus, in some implementations, the silicon septum (vial lid) or the first cover 126 comprising three apertures can be used to seal the extraction vial 120. For example, in some implementations, a first aperture is used for receiving the first capillary fiber of the CFLCT device 110, a second aperture is used for a second capillary tube 128, and a third aperture may be used for insertion of the sample injection site 118 into the extraction vial 120. In one implementation, the third aperture may be sealed and closed before vacuum pump 124 is turned on.

The remaining ends of the capillary tubes are attached to the peristaltic pump 112 for circulation of the analytes' vapors 130, which are release from the sample matrix by reducing pressure. Thus, by turning the vacuum pump 124 on, the extraction vial 120 is vacuumed. In some implementations, after the desired vacuum is reached, the vacuum pump 124 is detached from the extraction vial 120 by changing the position of the two-way valve 122 from an open position to a closed position and the sample injection site 118 is opened to inject the sample matrix 116. Thus, in one implementation, the valve disables the communication between the vacuum pump and the extraction vial in the closed position, and the valve enables the communication between the vacuum pump and the extraction vial in the open position.

The pressure gradient can cause the analytes to evaporate (for example, as vapor 130) from the sample matrix 116, and in some implementations, the nano sorbent 114 can adsorb the analyte. Furthermore, by turning on the peristaltic pump 112, the analyte vapors circulate inside the system 100 and the second capillary tube 128 for further adsorption on the nanosorbent 114.

The system 100 thus can be understood to include a first end, a second end, and a fiber positioned inside the system 100 between the first end and the second end. The fiber is coated with a sorbent (such as a nanosorbent). In one implementation, the nanosorbent may be removed from the capillary tube and inserted back into the capillary tube. As a result of the exertion from the pressure gradient, the analyte releases from the sample and enters the first end of the system 100 where it adsorbs on the nano-sorbent surface coated on the fiber. Unlike conventional methods where some sample preparation steps are required to extract the analytes, the system 100 can then be introduced into a conventional GC injector for sample desorption without further preparation steps.

It can be understood that there are many advantages of such a system. For example, there may be no solvents involved, and the total sampling and analysis time may be relatively short (about 15 minutes in some implementations)—a duration that is significantly less when compared to many existing methods. As such, the device can serve as a screening tool, in particular where a rapid analysis is needed or desired. In addition, such a device can serve as a time-weighted average sampler, where either continuous sampling over a long sampling time or a sequence of short sampling events within a required sampling period is used.

In some implementations, the system 100 may include a stainless-steel capillary tube. A fiber may be inserted into the capillary tube, and the nano sorbent may be coated on the fiber. In one exemplary implementation, the nano sorbent may be polypyrrole/graphene oxide (PPy/GO) nanocomposite. The PPy/GO nanocomposite may be synthesized via an electrochemical polymerization/electrophoretic deposition method on the fiber which may be inserted into the system 100 in one implementation.

Figure 2A:
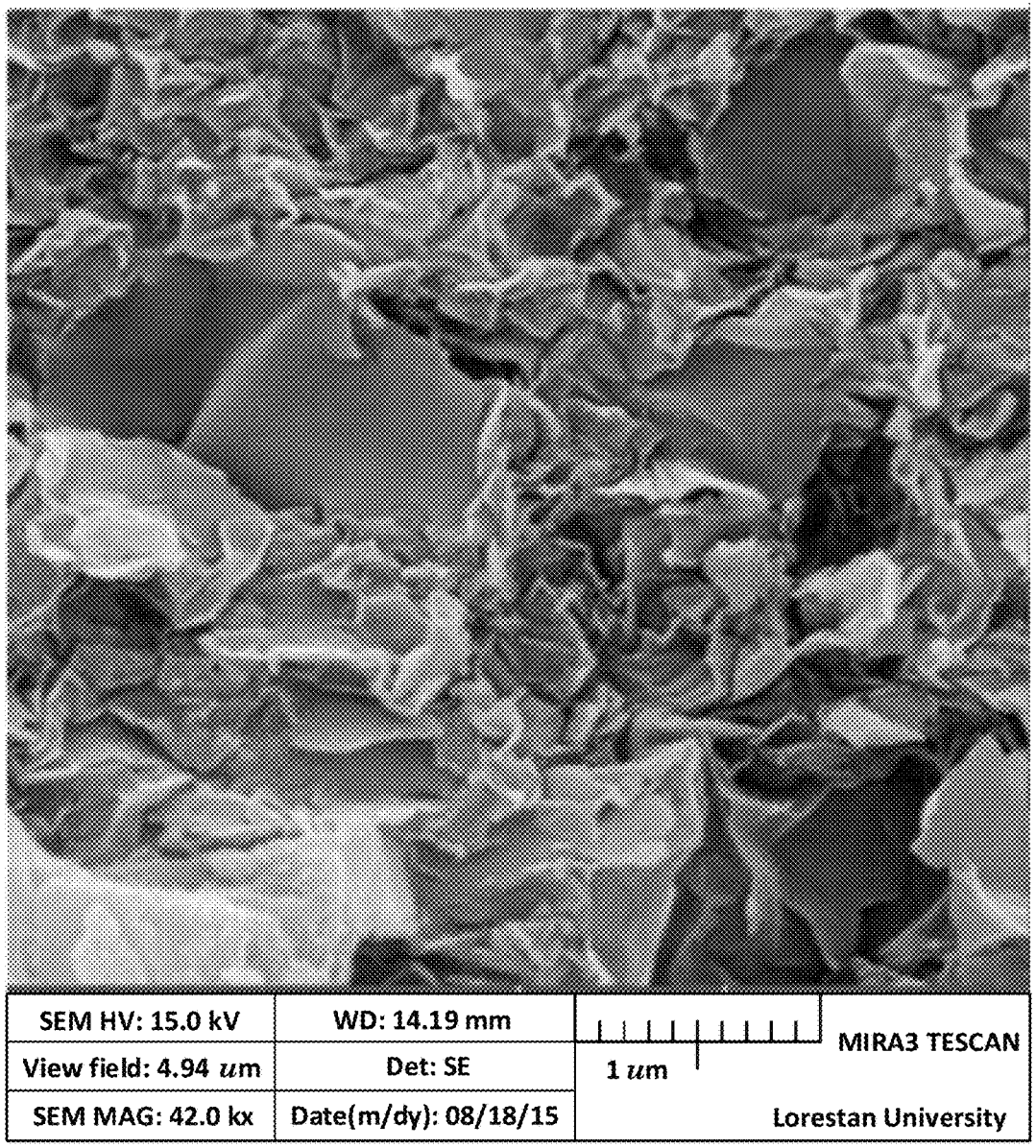
FIG. 2 illustrates scanning electron microscopy (SEM) images of the GO (a), PPy (b), and PPY/GO-coated fiber (c) in accordance with one implementation of the instant application.
Figure 2B:
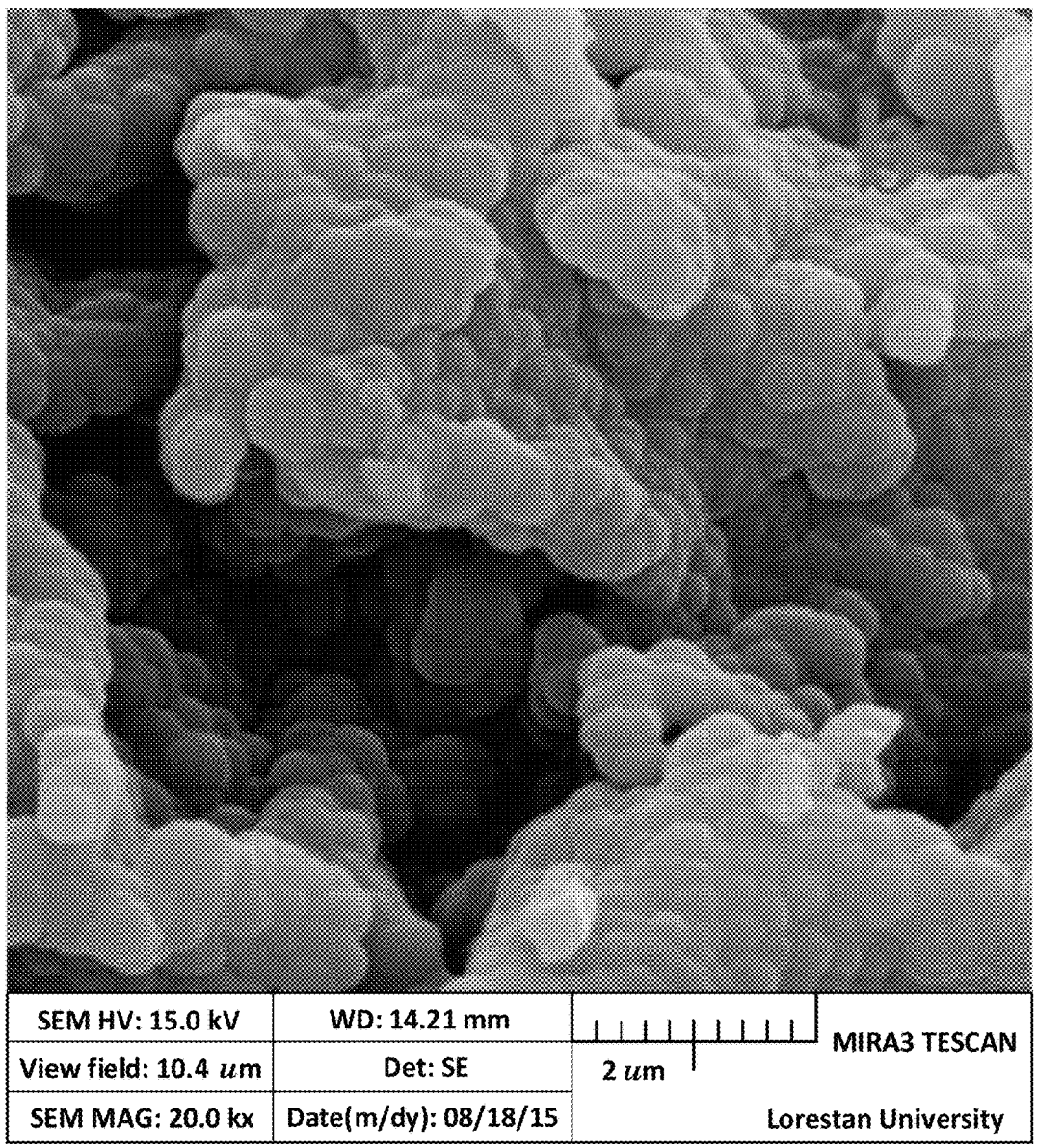
Figure 2C:
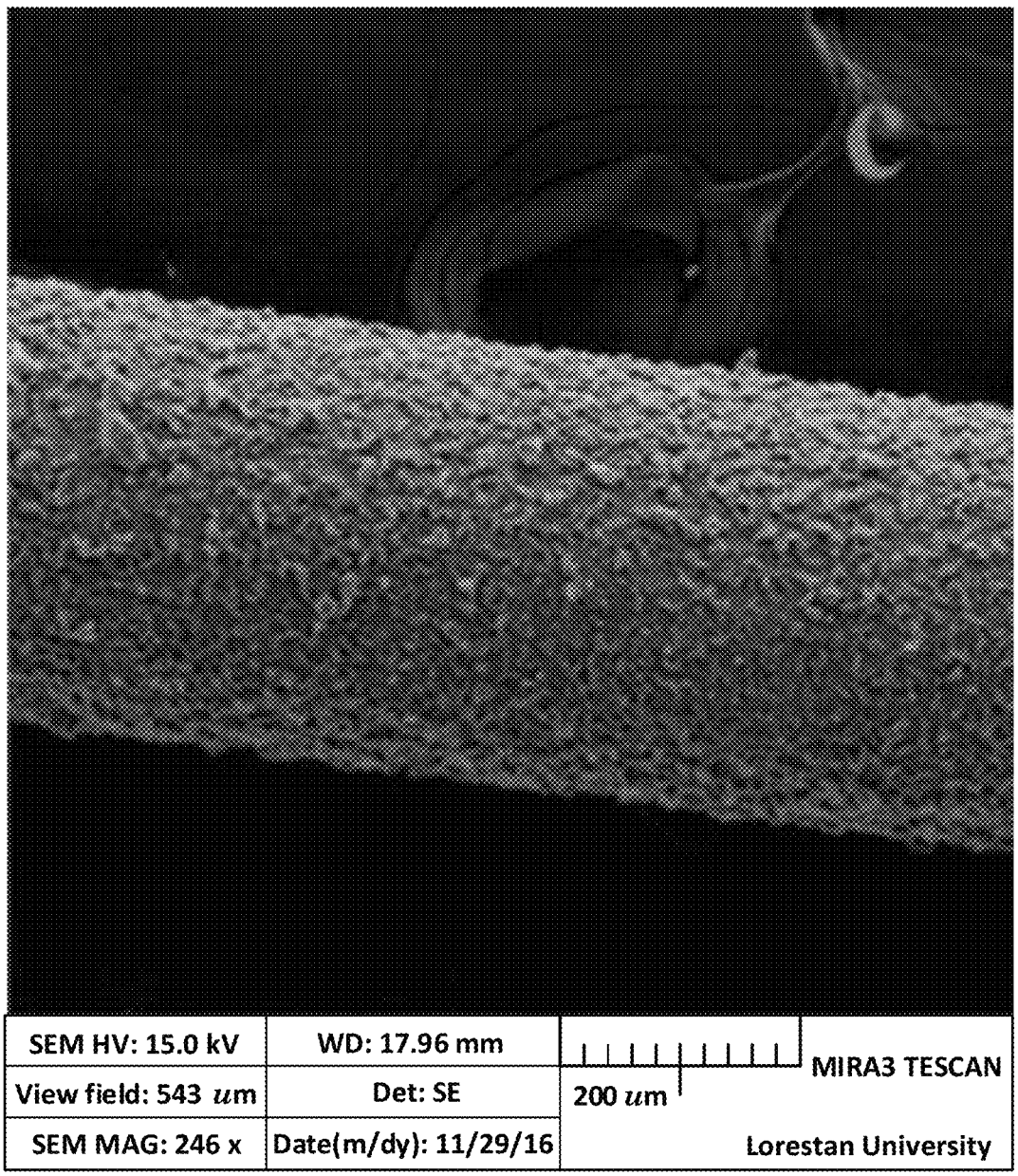
Figure 3:
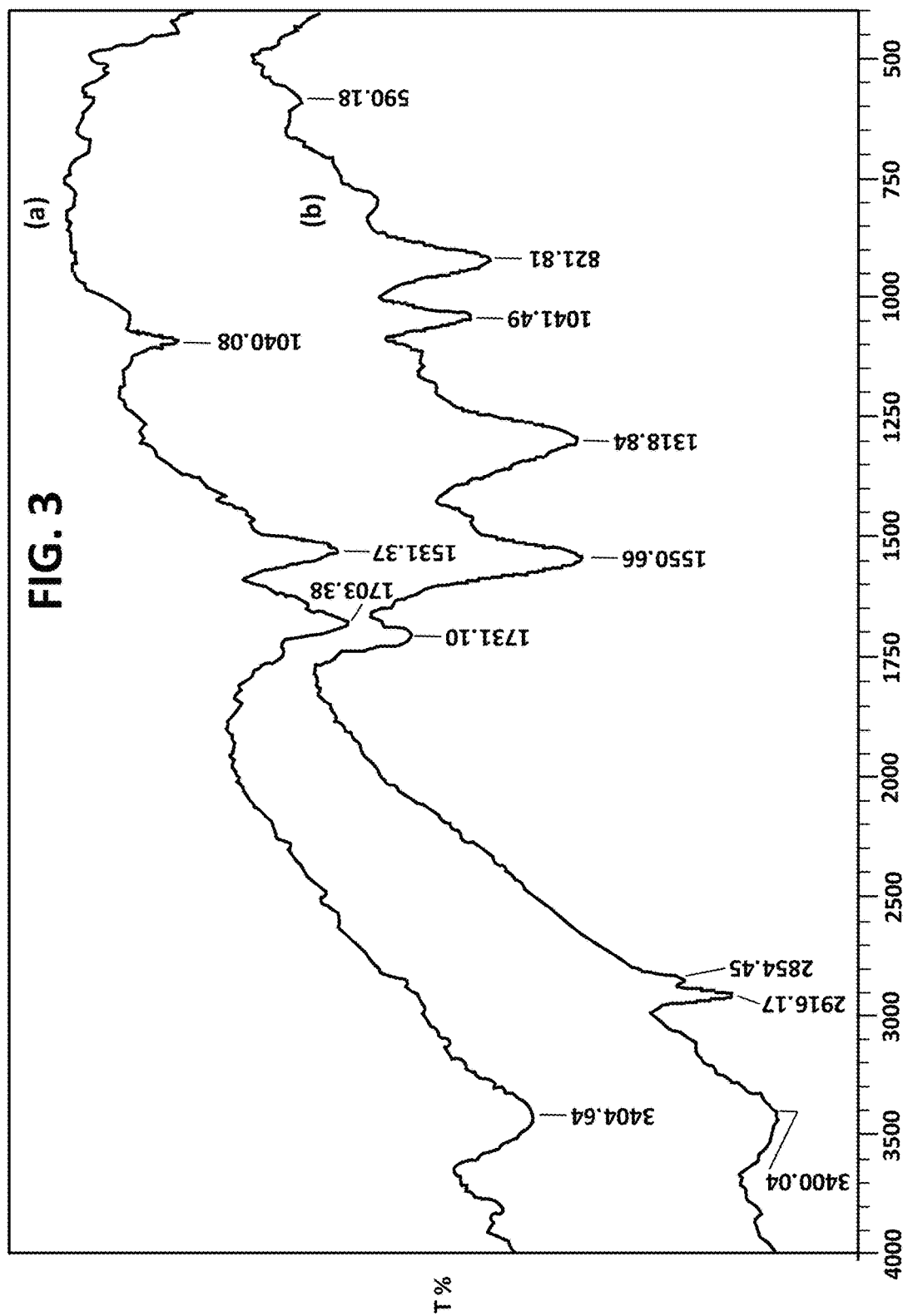
FIG. 3 illustrates FT-IR spectra of the nanocomposite sorbent of the fiber in accordance with one implementation of the instant application, (a) GO, (b) PPy/GO.

Referring now to FIG. 2, a scanning electron microscopy (SEM) image of the PPy/GO-coated fiber according to an example of the present application is provided. As shown in the image, the nanocomposite sorbent is uniformly distributed on surface of the fiber. FIG. 3 further illustrates an FT-IR of the nanocomposite sorbent of the present application and the fiber.

In one implementation, after extracting the analyte on the sorbent, the vacuum-assisted coated fiber located in the capillary tube device may be detached from the septum and attached to the injection port of a chromatograph such as a GC-FID to measure the analyte quantitatively. The free end of the capillary tube may be sealed by silicon septum to help prevent the carrier gas from purging. In one implementation, the limit of detection (LOD) of aldehyde compounds in edible oil samples was 0.0003-0.0005 µg/mL and the relative standard deviations (% RSD, n=5) were in the range of 3.6-9.0% with the concentration of 0.1 µg/mL. The results show that in optimal conditions, the linear correlation was in the concentration range 0.001-50 µg/mL. The results indicate that the VA-CFLCT-GC-FID is a very accurate and reliable method. It should be noted that, in all cases, no pretreatment (such as heating of the sample) was needed and the analysis was performed in a short period of time. Therefore, the present application may be used to extract volatile organic compounds (VOCs) such as aldehydes in edible oils in which the samples are sensitive to oxygen and temperature.

Figure 4:
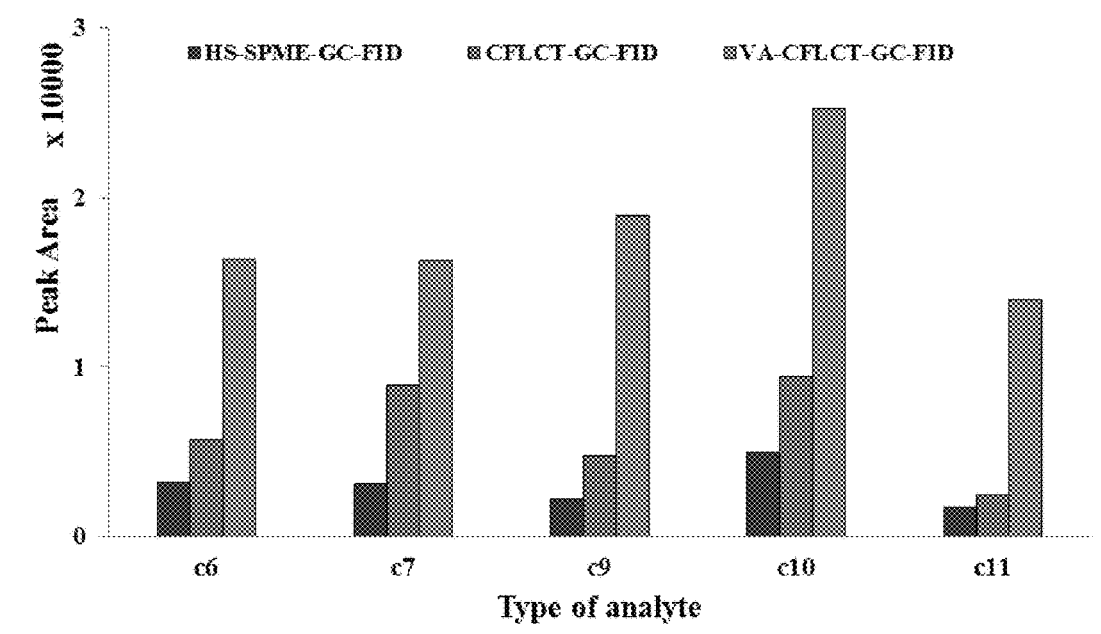
FIG. 4 illustrates a comparison between the extraction efficiency of the traditional SPME, CFLCT and VA-CFLCT methods coupled with GC-FID in accordance with one implementation of the instant application.

Referring now to FIG. 4, for purposes of clarity, a comparison between the extraction efficiency of the commercial SPME, CFLCT and an implementation of a VA-CFLCT device is presented in a graph. The devices were each coupled to the same GC-FID device. The samples are edible oils' aldehyde compounds. As shown in the graph, in all of the samples, the CFLCT-GC-FID extracts more aldehydes than SPME-GC-FID. Furthermore, the VA-CFLCT-GC-FID device of the disclosed implementations shows a significant improvement over both CFLCT-GC-FID and SPME-GC-FID devices.

Figure 5:
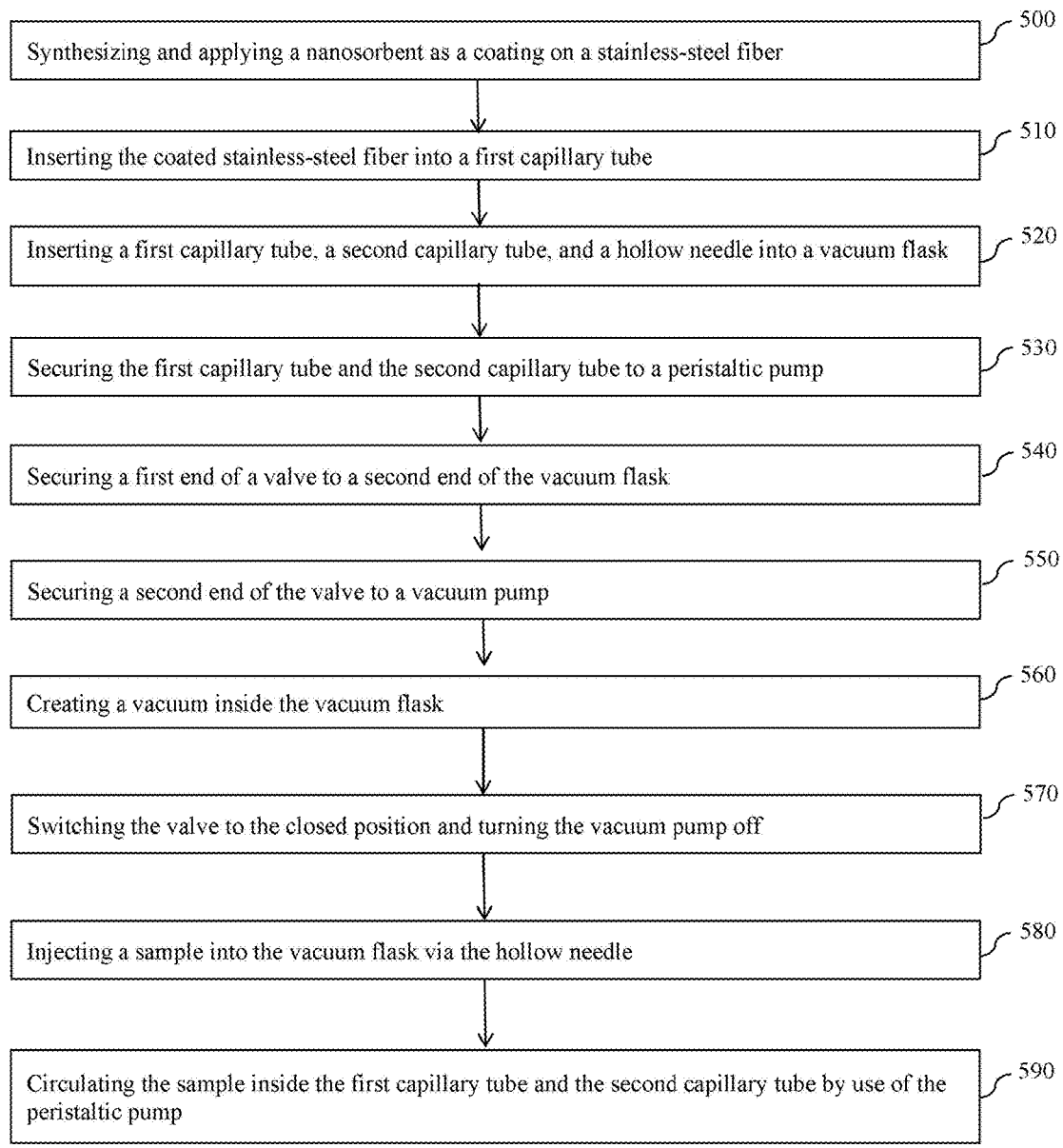
FIG. 5 illustrates a process of sampling utilizing the VA-CFLCT device according to an example of the instant application.

FIG. 5 illustrates a process of sampling with the VA-CFLCT device according to an implementation of the present application. In a first step 500, a sorbent or nanosorbent can be synthesized, and the nanosorbent can then be applied as a coating on at least a portion of a stainless-steel fiber. This can produce or result in a nanosorbent-coated stainless-steel fiber for use in the next step. In some implementations, the nanosorbent is synthesized via a 2-electrode electrochemical polymerization/electrophoretic deposition technique. Furthermore, in one implementation, the nanosorbent can include polypyrrole and graphene oxide nanocomposite. A second step 510 includes inserting the nanosorbent-coated stainless-steel fiber into a first capillary tube. In a third step 520, a first end of the first capillary tube is inserted into a first end of a vacuum flask via a first aperture. In addition, a first end of a second capillary tube is also inserted into the first end of the vacuum flask via a second aperture, as well as a hollow needle, which can be inserted into the first end of the vacuum flask via a third aperture. In some implementations, the first capillary tube and/or the second capillary tube can comprise stainless steel.

In a fourth step 530, a second end of the first capillary tube is secured or attached to a peristaltic pump, and a second end of the second capillary tube is secured or attached to the peristaltic pump. A fifth step 540 can comprise securing a first end of a valve to a second end of the vacuum flask. In some implementations, the being valve is configured to control a vacuum process. In one exemplary implementation, the valve includes an open position and a closed position to facilitate the vacuum process. A sixth step 550 includes securing a second end of the valve to a vacuum pump. In a seventh step 560, a vacuum can be created or formed inside the vacuum flask by turning on the vacuum pump and switching the valve to the open position. An eighth step 570 comprises switching the valve to the closed position and turning the vacuum pump off, thereby maintaining the vacuum inside the vacuum flask. In a ninth step 580, a sample is inserted or otherwise added into the vacuum flask via the hollow needle. A tenth step 590 involves circulating the sample inside the first capillary tube and the second capillary tube by use of the peristaltic pump. The circulation may facilitate adsorption of the analytes on the nanosorbent.

The separation of various components in the examples described above should not be understood as requiring such separation in all examples, and it should be understood that the described components and systems can generally be integrated together in a single packaged into multiple systems.

As described herein, the method provides for the fabrication of the VA-CFLCT-GC-FID system and allows for measurement of aldehydes. These measurements help evaluate the purification or oxidation rate of edible oils, which can be used to investigate and compare the oxidative stability of edible oils under reduced pressure and at room temperature (since they are sensitive to oxygen and temperature). Furthermore, the method may be utilized in the measurement of aldehydes in several edible oil samples and evaluation of oxidative resistance under optimal conditions. The system and method was also compared with a standard method and the results showed satisfactory agreement (see example below).

Thus, the various implementations of the method disclosed herein permit a rapid evaluation of the stability of oil oxidation, without additional heating, harmful solvents, manipulation, and/or repetitive sample preparation of the edible oil samples. Therefore, the CFLCT system can be understood to provide an effective, reliable, and sensitive method without the problems and limitations associated with the conventional SPME technique. Moreover, making use of a PPy/GO nanocomposite as a fiber coating in CFLCT, possessing a high ratio of surface to volume with high absorption capacity and low cost, increases the system's effectiveness and reliability.

Determination of Aldehydes in Edible Oil Samples by VA-CCFLCT-GC-FID

To investigate and evaluate the performance of the proposed method in the measurement of aldehydes, several edible oil samples were gathered from regional supermarkets and were analyzed with the VA-CFLCT-GC-FID method, without any sample preparation. The results were compared with results obtained from a validated method (see TABLE 1 below). A statistical t-test was applied to ensure reliability and provide support between the proposed method, and the validated method. With regard to the three times repetition for each oil sample, the experimental t Value for n=3 was obtained as 0.65 for each. The critical t value at a significant level (P=0.05) equaled 2.77. Regarding the experimental value, it should be understood that this is less than the critical value and there is no significant difference between two methods. Moreover, their accuracies are substantially equal.

TABLE 1

Extraction and determination of aldehydes in six edible oil samples using RPE-CTICF-GC-FID and a validated HS-SPME-GC-FID method

| | | Aldehydes determined ($\mu g\ g^{-1}$) | | | | | | | | |
|---|---|---|---|---|---|---|---|---|---|---|
| | Added | RP-CTICF-GC-FID | | | | | HS-SPME-GC-FID | | | |
| Oil sample | ($\mu g\ l^{-1}$) | Hex | Hep | Non | Dec | Undec | Hex | Hep | Non | Dec | Undec |
| Corn oil | 0 | 116 | 45 | 55 | 39 | 30 | 120 | 53 | 58 | ND | ND |
| | | (8.1)* | (6.0) | (6.3) | (5.7) | (6.9) | (7.6) | (8.2) | (9.3) | | |
| | 100 | 225 | 150 | 150 | 142 | 127 | 223 | 155 | 152 | 135 | 132 |
| | | (7.7) | (5.9) | (6.0) | (5.3) | (6.3) | (7.2) | (8.0) | (8.8) | (6.5) | (8.0) |
| Sunflower oil | 0 | 398 | 62 | 67 | 48 | 38 | 405 | 65 | 62 | 53 | 52 |
| | | (8.1) | (6.3) | (6.6) | (6.3) | (7.2) | (7.4) | (8.3) | (7.4) | (7.2) | (8.3) |
| | 100 | 500 | 155 | 174 | 150 | 140 | 510 | 162 | 158 | 159 | 156 |
| | | (7.3) | (6.1) | (6.8) | (6.0) | (7.0) | (7.1) | (8.7) | (8.0) | (7.1) | (6.3) |
| Soybean oil | 0 | 305 | 60 | 48 | 44 | 26 | 298 | 62 | 55 | 50 | ND |
| | | (9.0) | (6.4) | (7.3) | (5.4) | (7.7) | (6.3) | (7.4) | (8.3) | (7.9) | |
| | 100 | 400 | 154 | 143 | 138 | 132 | 390 | 158 | 159 | 144 | 128 |
| | | (8.6) | (6.2) | (7.2) | (5.0) | (7.2) | (6.2) | (6.8) | (8.7) | (8.3) | (6.0) |
| Olive oil | 0 | 402 | 118 | 92 | 87 | 69 | 400 | 125 | 100 | 85 | 65 |
| | | (7.8) | (7.1) | (6.8) | (5.6) | (6.8) | (7.2) | (7.3) | (6.0) | (7.5) | (8.6) |
| | 100 | 498 | 223 | 190 | 186 | 173 | 506 | 220 | 196 | 183 | 160 |
| | | (7.5) | (6.0) | (7.0) | (5.2) | (7.1) | (7.6) | (6.6) | (8.3) | (7.4) | (7.3) |

TABLE 1-continued

Extraction and determination of aldehydes in six edible oil samples using RPE-CTICF-GC-FID and a validated HS-SPME-GC-FID method

| | | Aldehydes determined (µg g$^{-1}$) | | | | | | | | |
|---|---|---|---|---|---|---|---|---|---|---|
| | Added | RP-CTICF-GC-FID | | | | | HS-SPME-GC-FID | | | |
| Oil sample | (µg l$^{-1}$) | Hex | Hep | Non | Dec | Undec | Hex | Hep | Non | Dec | Undec |
| Canola oil | 0 | 276 | 48 | 44 | 43 | 32 | 272 | 55 | ND | 50 | ND |
| | | (8.4) | (6.9) | (7.3) | (5.7) | (7.4) | (7.7) | (6.9) | | (5.1) | |
| | 100 | 380 | 143 | 142 | 152 | 130 | 378 | 150 | 140 | 155 | 137 |
| | | (8.2) | (7.3) | (6.5) | (5.0) | (6.5) | (8.4) | (6.0) | (7.9) | (8.0) | (7.8) |
| Sesame oil | 0 | 93 | 33 | 41 | 28 | 30 | 88 | ND | 52 | ND | ND |
| | | (8.5) | (6.1) | (6.3) | (6.0) | (6.5) | (7.9) | | (6.9) | | |
| | 100 | 201 | 137 | 135 | 131 | 133 | 192 | 130 | 142 | 125 | 128 |
| | | (8.3) | (7.2) | (6.0) | (5.8) | (6.8) | (8.0) | (7.4) | (8.1) | (6.5) | (8.2) |

*The numbers in parentheses refer to RSD % obtained by three replicated analyses.

Furthermore, the RP-FIN-GC-FID method was used to measure the content of hexanal in several samples of edible oils which were kept at 25° C., 70° C. and 110° C. at three different time points. Based on the results (see TABLE 2 below) the oxidation stabilities of each were evaluated and compared. By analyzing the increasing rate of hexanalin edible oils at different temperatures over a duration of 45 days (as shown in TABLE 2), it can be seen that sunflower oil and sesame oil have the lowest and highest oxidative stability, respectively. That is, in cases of heating and/or storage, sunflower oil has a higher rate of hexanal production relative to other oils. In addition, sesame oil experiences the lowest rate of hexanal production during heating and/or storage. Oil oxidation and hexanal production can be understood to correspond to an amount of polyunsaturated fatty acids in the oils. Due to the ability of the oil's unsaturated fatty acid to oxidize in the vicinity of oxygen and varying temperatures, as well as the higher percentage of polyunsaturated fatty acids in the profile of the edible oil, the resistance to oxidation is lower. Thus, sunflower oil has the lowest oxidation resistance due to the highest percentage of polyunsaturated fatty acid (65-70%), whereas sesame oil has the highest oxidation resistance in this case due to the presence of low polyunsaturated fatty acids and the presence of a ligand and, natural antioxidant. This information can be readily obtained through the RP-FIN-GC-FID method, in a relatively short period of time, and without the use of toxic solvents.

TABLE 2

Determination of hexanal in edible oils which were kept in different time at 25, 70 and 110° C. using RP-CTICF-GC-FID method and evaluated of their oxidation stability

| | | Determined hexanal by RP-CTICF-GC-FID method Oil sample | | | | | |
|---|---|---|---|---|---|---|---|
| Storage temperature (° C.) | Storage time (day) | Corn oil | Sunflower oil | soybean oil | Olive oil | Canola oil | Sesame oil |
| 25 | 0 | 116 | 398 | 305 | 402 | 276 | 93 |
| | 15 | 125 | 415 | 315 | 420 | 310 | 101 |
| | 30 | 138 | 432 | 335 | 431 | 328 | 108 |
| | 45 | 159 | 450 | 344 | 438 | 349 | 114 |
| 70 | 0 | 116 | 398 | 305 | 402 | 276 | 93 |
| | 15 | 2050 | 5083 | 2934 | 1834 | 2564 | 880 |
| | 30 | 4278 | 10266 | 7468 | 5324 | 6483 | 1477 |
| | 45 | 7682 | 17749 | 12826 | 7826 | 11925 | 2423 |
| 110 | 0 | 116 | 398 | 305 | 402 | 276 | 93 |
| | 15 | 3484 | 9620 | 6938 | 4268 | 5885 | 1823 |
| | 30 | 7639 | 23342 | 13810 | 8925 | 12434 | 3718 |
| | 45 | 11373 | 36932 | 23047 | 12834 | 19981 | 5943 |

*The numbers in parentheses refer to RSD % obtained by three replicated analyses.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations for the purpose of streamlining the disclosure. This method of disclosure is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

What is claimed is:

1. A vacuum-assisted coated fiber located in a capillary tube (VA-CFLCT) system comprising:
    a first capillary tube including a first end and a second end;
    a second capillary tube disposed adjacent to the first capillary tube;
    a stainless-steel fiber disposed in an interior space of the first capillary tube;
    an extraction vial including a first opening and a second opening, the extraction vial configured for extraction of an analyte;
    a sorbent coated on the stainless-steel fiber, the sorbent being configured to entrap the analyte, the analyte being attached to a sample that is injected into the extraction vial;
    a first cover configured to cover the first opening of the extraction vial, the first cover including a first aperture, a second aperture, and a third aperture, the first aperture being configured to receive the first capillary tube within an interior space of the extraction vial, the second aperture being configured to receive the second capillary tube within the interior space of the extraction vial, and the third aperture being configured to receive a hollow needle for injecting the sample into the extraction vial;
    a pump including an inlet and an outlet, the inlet coupled to the second end of the first capillary tube, the pump being configured to circulate the extracted analyte though the first capillary tube and the second capillary tube to improve analyte adsorption on the sorbent inside the first capillary tube; and
    a vacuum device configured to evacuate the interior space of the extraction vial and improve the efficiency of the analyte extraction process, wherein:
    the vacuum device includes a valve and a vacuum pump,
    a connection tube is configured to connect the vacuum pump to the second opening of the extraction vial,
    the vacuum pump is in fluid communication with the extraction vial and is configured to provide a vacuum within the interior space of the extraction vial, and
    the valve being configured to operate between an open position and a closed position, wherein in the closed position the valve disables communication between the vacuum pump and the extraction vial and in the open position the valve enables the communication between the vacuum pump and the extraction vial.

2. The system of claim 1, wherein the sorbent is polypyrrole and graphene oxide nanocomposite.

3. The system of claim 1, wherein the sorbent is made by a 2-electrode electrochemical polymerization/electrophoretic deposition technique.

4. The system of claim 1, wherein the first capillary tube comprises stainless steel.

5. A method for sampling analytes comprising:
    synthesizing a nanosorbent;
    applying the nanosorbent as a coating on at least a portion of a stainless-steel fiber, thereby producing a nanosorbent-coated stainless-steel fiber;
    inserting the nanosorbent-coated stainless-steel fiber into a first capillary tube reinforced by a vacuum system;
    inserting a first end of the first capillary tube into a first end of a vacuum flask via a first aperture;
    inserting a first end of a second capillary tube into the first end of the vacuum flask via a second aperture;
    inserting a hollow needle into the first end of the vacuum flask via a third aperture;
    securing a second end of the first capillary tube to a peristaltic pump;
    securing a second end of the second capillary tube to the peristaltic pump;
    securing a first end of a valve to a second end of the vacuum flask, the being valve configured to control a vacuum process, the valve including an open position and a closed position;
    securing a second end of the valve to a vacuum pump;
    creating a vacuum inside the vacuum flask by turning on the vacuum pump and switching the valve to the open position;
    switching the valve to the closed position and turning the vacuum pump off, thereby maintaining the vacuum inside the vacuum flask;
    injecting a sample into the vacuum flask via the hollow needle; and,
    circulating the sample inside the first capillary tube and the second capillary tube by use of the peristaltic pump.

6. The method of claim 5, wherein the nanosorbent is a polypyrrole and graphene oxide nanocomposite.

7. The method of claim 5, wherein the nanosorbent is made by a 2-electrode electrochemical polymerization/electrophoretic deposition technique.

8. The method of claim 5, wherein at least the first capillary tube comprises stainless steel.

* * * * *